(12) United States Patent
Bamberg et al.

(10) Patent No.: US 11,771,843 B2
(45) Date of Patent: Oct. 3, 2023

(54) SYRINGE AND METHOD OF PREPARING SYRINGE

(71) Applicants: Hoffmann-La Roche Inc., Little Falls, NJ (US); GENENTECH, INC., South San Francisco, CA (US)

(72) Inventors: Frank Bamberg, Schopfheim (DE); Heather L. Flores, Hayward, CA (US); Robert Müller, Weil am Rhein (DE); Elisabeth Schaible, Basel (CH); Edward Schwarb, Basel (CH); Lionel Vedrine, Palo Alto, CA (US); Kewei Yang, Basel (CH); Mathieu Rigollet, Saint-Louis (FR); Pierre Goldbach, Mulhouse (FR); Baboo Dushyantsingh Goordyal, Basel (CH); Ivy Lin, South San Francisco, CA (US); Florian Wildenhahn, Basel (CH)

(73) Assignees: HOFFMANN-LA ROCHE INC., Little Falls, NJ (US); GENENTECH, INC., South San Francisco, CA (US)

( * ) Notice: Subject to any disclaimer, the term of this patent is extended or adjusted under 35 U.S.C. 154(b) by 0 days.

(21) Appl. No.: 17/675,509

(22) Filed: Feb. 18, 2022

(65) Prior Publication Data
US 2022/0203041 A1    Jun. 30, 2022

Related U.S. Application Data

(62) Division of application No. 15/523,048, filed as application No. PCT/EP2015/075302 on Oct. 30, 2015, now abandoned.
(Continued)

(51) Int. Cl.
*A61M 5/32* (2006.01)
*A61M 5/00* (2006.01)
(Continued)

(52) U.S. Cl.
CPC ........... *A61M 5/3202* (2013.01); *A61L 31/10* (2013.01); *A61L 31/16* (2013.01); *A61M 5/002* (2013.01);
(Continued)

(58) Field of Classification Search
CPC .... A61M 2005/312; A61M 2205/0238; A61M 5/002; A61M 5/32
See application file for complete search history.

(56) References Cited

U.S. PATENT DOCUMENTS 4,964,866 A      10/1990  Szwarc
5,851,200 A  *  12/1998  Higashikawa ............ B44F 1/14
                                                              604/199
(Continued)

FOREIGN PATENT DOCUMENTS

EP      0709105        5/1996
JP      H08-243161 A   9/1996
(Continued)

OTHER PUBLICATIONS

Militaerstrasse, "Datwyler Sealing Solutions," 2013, Datwyler Inc, p. 1-5 <http://sealing.datwyler.com/en/compund-formulations>. Accessed Aug. 3, 2020 (Year: 2013).
(Continued)

*Primary Examiner* — William R Carpenter
(74) *Attorney, Agent, or Firm* — MEDLER FERRO WOODHOUSE & MILLS PLLC

(57) ABSTRACT

A syringe (18) has a longitudinal body (28) with an interior (228) in which a pharmaceutical substance is arranged, a needle connected to one longitudinal end of the body (228) and a rigid needle shield (38) encasing the needle. The rigid needle shield (38) is essentially water vapour tight. The syringe (18) according to the invention allows for preventing needle clogging and, thus, proper provision of pharmaceu-
(Continued)

ticals, particularly by subcutaneous, intramuscular or ocular injection.

13 Claims, 2 Drawing Sheets

Related U.S. Application Data

(60) Provisional application No. 62/072,625, filed on Oct. 30, 2014.

(51) Int. Cl.
| | |
|---|---|
| *A61L 31/10* | (2006.01) |
| *A61L 31/16* | (2006.01) |
| *A61M 5/315* | (2006.01) |
| *B65B 3/00* | (2006.01) |
| *B65B 7/16* | (2006.01) |
| *A61M 5/178* | (2006.01) |

(52) U.S. Cl.
CPC ............ *A61M 5/315* (2013.01); *A61M 5/329* (2013.01); *B65B 3/006* (2013.01); *B65B 7/16* (2013.01); *A61M 5/178* (2013.01); *A61M 2205/0216* (2013.01); *A61M 2205/0238* (2013.01); *A61M 2207/00* (2013.01)

(56) References Cited

U.S. PATENT DOCUMENTS

| | | | |
|---|---|---|---|
| 6,331,174 | B1 | 12/2001 | Reinhard |
| 6,551,286 | B1 | 4/2003 | Claessens |
| 2002/0062108 | A1 | 5/2002 | Courteix |
| 2003/0040706 | A1 | 2/2003 | Kuracina |
| 2004/0267194 | A1 | 12/2004 | Sano |
| 2005/0038391 | A1 | 2/2005 | Wittland |
| 2005/0075611 | A1 | 4/2005 | Hetzler et al. |
| 2011/0060290 | A1 | 3/2011 | Bonk |
| 2012/0014968 | A1* | 1/2012 | Walsh ............... A61J 1/065 222/386 |
| 2013/0200549 | A1 | 8/2013 | Felts |
| 2014/0262883 | A1* | 9/2014 | Devouassoux ........ B65D 75/36 206/364 |
| 2015/0273133 | A1 | 10/2015 | Kerschbaumer et al. |
| 2016/0151584 | A1 | 6/2016 | Deleuil |
| 2017/0296757 | A1 | 10/2017 | Maeda |
| 2018/0133375 | A1 | 5/2018 | Shiozaki |

FOREIGN PATENT DOCUMENTS

| | | |
|---|---|---|
| JP | 2004-525712 A | 8/2004 |
| JP | 2006-231859 A | 9/2006 |
| JP | 2013-043957 A | 3/2013 |
| WO | 02/083231 A1 | 10/2002 |
| WO | 2014/053560 A1 | 4/2014 |
| WO | 2014059012 A1 | 4/2014 |
| WO | 2016052037 A1 | 4/2016 |
| WO | 2016068333 A1 | 5/2016 |

OTHER PUBLICATIONS

Notice of Reasons for Refusal issued in Japanese Application No. 2017-523258 dated Sep. 5, 2019.

Stemli, "A Rigid Needle Shield for Auto-Injectors," 2011, Frederick Furness Publishing, <http://www.ondrugdelivery.com/publications/Injectable%20Devices%202011/Stemlmi.pdf>. Accessed Feb. 15, 2019 (Year: 2011).

O'Malley, John, "Baxter's BioPharma Solutions Business Expanding Diluent Prefilled Syringe Offering," 2014, BioPharma Solutions, <http://www.thepromisofscience.com/pdf/920898_Baxter_Diluent_newsrelease.pdf>. Accessed Feb. 15, 2019 (Year:2014).

Furness, Guy, "Prefilled Syringes". 2016, Frederick Furness Publishing, <https://www.ondrugdelivery.com/publications/71/Issue_71_Hi_Res.pdf>. Accessed Feb. 15, 2019 (Year: 2016).

Aptar, "Elastometric Formulations for Pre-Filled Syringes and Cartridges," 2016, https://pharma.antar.com/sites/default/files/products/marketing_sheet/files/pds_formulations_for_pfsandcartridges.pdf>. Accessed Feb. 15, 2019 (Year: 2016).

International Search Report and Written Opinion issued in International Application No. PCT/EP2015/075302, dated Feb. 12, 2016.

\* cited by examiner

SYRINGE AND METHOD OF PREPARING SYRINGE

TECHNICAL FIELD

The present invention relates to a syringe according to the preamble of independent claim 1 and more particularly to a method of preparing an according syringe. Such a syringe having a longitudinal body with an interior in which a pharmaceutical substance is arranged, a needle connected to one longitudinal end of the body and an elastomeric needle cap encasing the needle can be used for providing and applying the pharmaceutical substance to a patient.

BACKGROUND ART

Many pharmaceutical products are applied to patients in liquid form wherein injecting the product often is most efficient and preferred. Particularly for subcutaneous, intramuscular, intradermal or intravitreal injection the pharmaceutical substances are often provided in pre-filled syringes wherein staked-in needle prefilled syringes have been shown to be comparably convenient to handle and use. In such syringes the pharmaceutical substance is provided in the interior of the syringe in a solved form ready for being applied. Like this, the user receives a ready-to-inject syringe without the requirement to fill the pharmaceutical solution into the syringe or to manually assemble the needle to the syringe body. The occurrence of injuries or inappropriate handling during application can thereby be minimized.

Usually, staked-in needle pre-fillable syringes consist of a syringe body, a staked-in needle and a rigid needle shield (RNS). The RNS is the closure of the needle which aims for preventing accidental stick injuries, leaking of pharmaceutical substance and entry of contaminations. Commonly, RNS have an inner elastomeric part which is adjacent to and incorporates the needle and an outer solid part which can be made of a thermoset plastic material or the like.

For preparing such a staked-in needle pre-fillable syringe the syringe is typically pre-sterilized such that it is ready-to-fill before filling the pharmaceutical substance. The sterilization process is normally done by ethylene oxide gas or other ways of sterilization. Ethylene oxide sterilization requires gas permeability of the rigid needle shield in order to sterilize the needle surface. Therefore, the rigid needle shield often possesses significant gas permeability for other gases including water vapour. After pre-sterilization the pharmaceutical substance is provided into an interior of the syringe body and the proximal opening of the syringe body is closed by an elastomeric plunger.

In staked-in needle (SIN) pre-filled syringes (PFS) as described hereinbefore some pharmaceutical substances tend to clog particularly in or near the needle such that the pharmaceutical substance cannot be properly pushed throughout the syringe anymore. In particular, where the pharmaceutical substance is a biopharmaceutical substance and, for example, comprises a protein at a comparably high concentration, clogging can be induced by aggregates or precipates formed by the protein. Such clogging is undesirable because it can prevent patients from receiving full doses of pharmaceutical substances or medications. Thus, prevention of needle clogging can be crucial for allowing provision of the biopharmaceutical substance in a SIN-PFS.

Therefore, there is need for a system allowing for minimizing or eliminating clogging of a needle of a, e.g. staked-in needle, pre-filled syringe and thereby allowing for a proper provision of pharmaceuticals and particularly biopharmaceuticals with or without proteins via the pre-filled syringe.

Disclosure of the Invention

According to the invention this need is fulfilled by a syringe and a method as described herein. Preferred embodiments are subject of the claims.

In particular, in one embodiment, the invention is a syringe that has a longitudinal body with an interior in which a, typically liquid, pharmaceutical substance is arranged, a needle connected to one longitudinal end of the body and a rigid needle shield encasing the needle. Thereby, the rigid needle shield is water vapour tight.

The term "rigid needle shield" or RNS as used herein can relate to a closure which covers the needle. It prevents accidental needle stick injuries and serves as a closure which prevents leaking of the drug product solution and entry of microbiological or other contaminations.

The term "water vapour tight" as used herein can relate to no or a comparably low permeability for water vapour. Comparably low permeability in this context can relate to a permeability of 1.2 gram per squared meter and day $$\left(\frac{g}{m^2 \times d}\right)$$

water vapour at 5 degree Celsius (° C.) and 60% relative humidity (rh) or less and of $$1.3 \frac{g}{m^2 \times d}$$

water vapour at 25° C. and 60% rh or less and of $$1.5 \frac{g}{m^2 \times d}$$

water vapour at 4° C. and 75% rh or less. A material or assembly fulfilling these conditions can be water vapour tight in the present context.

The syringe body can be made from any inert material having suitable properties with respect to rigidity and usability. For example, it can be made of or comprise glass. In another example, it can be made of or comprise plastics.

During manufacturing, storage, transportation and use staked-in needle pre-filled syringes are exposed to different environmental conditions including elevated temperature, lower relative humidity and reduced atmospheric pressure. Specifically, the atmospheric pressure differential and water vapour pressure differential between the interior of the body of the syringe and the environment can lead to entry of the pharmaceutical substance into the needle and to evaporation by water vapour transfer through commonly known rigid needle shields. Thereby, the pharmaceutical substance or solution in the needle can solidify by drying or the like.

In accordance with the invention, the problem of needle clogging in pre-filled syringes can be solved or prevented by a modification of the rigid needle shield. In this context, the term "clogging" can refer to needle clogging being a blockage of the needle preventing or substantially reducing ejection of the pharmaceutical substance out of the syringe.

As explained in more detail by ways of the examples below, such rigid needle shield allows substantially decreasing or even eliminating the occurrence of needle clogging. Thus, the pre-filled syringe according to the invention allows for proper administration of pharmaceuticals, particularly by subcutaneous, intramuscular, ocular, intradermal or intravitreal injection.

Preferably, a needle neighbouring part of the rigid needle shield being adjacent to the needle has a low leaching capacity, particularly a low Zinc (Zn) leaching capacity. In connection with needle clogging in syringes, in addition to the relevance of the water vapour permeability of the rigid needle shield, the pharmaceutical solution in the needle can also solidify by interaction with leachable material from the material of the rigid needle shield. More specifically, Zinc ions which can leach from the part of the rigid needle shield neighbouring the needle, which conventionally is an elastomer part, can interact with the pharmaceutical substance or components thereof such as proteins. Such leachable or Zinc ion induced interaction can lead to a comparably strong increase of the viscosity of the pharmaceutical substance which can induce or produce clogging in the needle.

Therefore, providing the needle neighbouring part of the rigid needle shield in a material that is designed for substantially not leaching or that has a low leaching capacity, in particular related to Zinc, can prevent such increase of the viscosity. In this context, the term "low leaching capacity" or "low Zinc leaching capacity" can relate to a material or part leaching to an extent that the viscosity of the pharmaceutical substance is not or substantially not affected. More particular, a material can have such low Zinc leaching capacity if it has a maximum release of 5 μg Zinc ions per day and needle neighbouring part after incubation for 1 day at 25° C. in 1 mL of a 20 mM histidine-HCl, 100 mM arginine-HCl, 30 mM L-methione, 0.02% polysorbate 80, pH 6.0±0.5 aqueous solution. Thereby, the needle neighbouring part of the rigid needle shield is cut into 4 equal sized pieces.

Thus, such water vapour tight rigid needle shield having reduced water vapour permeability also has a reduced leaching, in particular of Zinc ions. The preferred improved rigid needle shield therefore possesses the combined properties of reduced permeability for water vapour and the reduced leaching of material or components, specifically Zinc ions.

Preferably, the rigid needle shield comprises a water vapour tight coat. Such a vapour tight coat can be arranged as an outer shell of the rigid needle shield. It allows for adapting a common syringe in order to implement a syringe in according with the invention having a reduced tendency of needle clogging. In particular, this allows for efficiently preparing syringes essentially in accordance with known systems and to add the coat as vapour barrier separately.

In one preferred embodiment, the coat comprises wax that can be selected from organic wax. Adding wax to the needle cap allows for efficiently providing the water vapour barrier to the rigid needle shield. It also allows for adapting conventionally prepared syringes in order to provide it with increased properties regarding the prevention of needle clogging. Materials other than wax are similarly possible for being applied to conventionally prepared syringes.

In another preferred embodiment, the coat additionally or alternatively comprises a water vapour tight pouch filled with an aqueous fluid. For example, the pouch can be made of aluminium. The aqueous fluid can particularly be water or a water like solution. Inside the pouch a suitable matrix such as a cotton ball can be arranged for gathering or holding the aqueous solution. Providing the syringe with a filled pouch is an alternative way of efficiently providing the water vapour barrier to the rigid needle shield and it also allows for adapting conventionally prepared syringes in order to provide it with better properties regarding the prevention of needle clogging.

As an alternative to the coat, the rigid needle shield preferably comprises a needle neighbouring part being adjacent to the needle which is made of a water vapour tight material. Such a rigid needle shield allows for an efficient one step provision of the water vapour barrier to the needle.

Thereby, the water vapour tight material preferably is ethylene propylene diene methylene based thermoplastic elastomer. Such a material allows for providing a vapour tight barrier which on one hand is not water permeably enough for allowing significant needle clogging and on the other hand is gas permeable enough for still allowing conventional sterilization of the needle such as, e.g., by ethylene oxide gas sterilization. It also allows an efficient manufacture or preparation of the syringe.

Alternatively, the water vapour tight material preferably is styrene-butadiene rubber compound free from 2 mercaptobenzothiazole. Such a material also allows for providing a vapour tight barrier which on one hand is not water permeably enough for allowing significant needle clogging and on the other hand is gas permeable enough for still allowing conventional sterilization of the needle such as, e.g., by ethylene oxide gas sterilization. Furthermore, it allows an efficient manufacture or preparation of the syringe.

Preferably, the interior of the body is sealed at a side opposite to the needle by a plunger. The plunger can be made of or comprise an elastic material or an elastic plastic material such as fluoro resin laminated butyl rubber. Such a plunger allows for safely sealing the interior of the body. Further, it can be easily pushed into the proximal opening of the needle body which allows for an efficient preparation of the syringe. Still further, it can be further pushed by an activation rod into the direction of the needle in order to provide the pharmaceutical substance out of the needle. Also, butyl rubber plungers do not significantly leach Zinc which can be additionally beneficial.

Preferably, the needle is integral with the syringe body. Such syringes are also referred to as staked-in needle syringes. They can comparably efficiently be manufactured. Also, they can be comparably easy to handle, e.g. in auto-injection, since it is not required to mount the needle before application.

Preferably, the pharmaceutical substance is a biopharmaceutical substance. The term "biopharmaceutical substance" can relate to any biologic therapeutic formulation in a liquid from. Many biopharmaceutical substances comprise comparably large molecules and have a comparably high tendency for clogging such that providing a vapour tight barrier and/or a reduced capacity for leaching, particularly Zinc leaching, to a rigid needle shield of respective syringe can be particularly useful.

Thereby, the biopharmaceutical substance preferably comprises a protein. The protein can, e.g., be a monoclonal antibody or the like. Within biopharmaceutical substances such substances can have an even higher tendency for clogging such that, again, providing a vapour tight barrier and/or a reduced capacity for leaching, particularly Zinc leaching, to a needle of respective syringe can be particularly useful.

Thereby, the substance preferably comprises the protein at a concentration in a range of about 50 mg/ml to about 250 mg/ml or to about 300 mg/ml. In this context, the abbreviation "mg" relates to milligram and the abbreviation "ml" to millilitre. In syringes with biopharmaceutical substances having proteins within such a range clogging easily and often occurs wherein it has been shown that the water vapour tight rigid needle shield according to the invention is particularly effective for preventing such clogging.

Another aspect of the present invention relates to a method of preparing a syringe having a longitudinal body with an interior and a needle connected to one longitudinal end of the body. The method comprises the steps of: filling a pharmaceutical substance inside the interior of the body of the syringe; sealing the interior of the body of the syringe by pushing a plunger through an opening embodied at a longitudinal end of the body opposite to the needle; and encasing the needle with a water vapour tight rigid needle shield. Such a method allows for efficiently preparing a syringe having the effects and benefits described hereinbefore.

Preferably, encasing the needle with the rigid needle shield comprises covering a needle cap with a water vapour tight coat. Such a coat can be wax or a pouch filled with a liquid as described hereinbefore.

The present disclosure also comprises the following embodiments of syringes:

Embodiment 1 is a syringe having a longitudinal body with an interior in which a pharmaceutical substance is arranged, a needle connected to one longitudinal end of the body and a rigid needle shield encasing the needle, wherein a needle neighbouring part of the rigid needle shield being adjacent to the needle has a low leaching capacity such as a low Zinc leaching capacity. As mentioned above, in connection with needle clogging in syringes, in addition to the relevance of the water vapour permeability of the rigid needle shield, the pharmaceutical solution in the needle can also solidify by interaction with leachable material from the rigid needle shield. More specifically, material or components such as Zinc ions which can leach from the part of the rigid needle shield neighbouring the needle, which conventionally is an elastomer part, can interact with the pharmaceutical substance or components thereof such as proteins. Such Zinc ion or leachable material induced interaction can lead to a comparably strong increase of the viscosity of the pharmaceutical substance which can induce clogging of the needle. Therefore, providing the needle neighbouring part of the rigid needle shield in a material that does leach, particularly leach Zinc, to no substantial extent or that has the low leaching or Zinc leaching capacity can prevent such increase of the viscosity regardless if the rigid needle shield is water vapour tight or not. In this context, the term "low leaching capacity" or "low Zinc leaching capacity" can relate to a material or part leaching material or components such as Zinc to an extent that the viscosity of the pharmaceutical substance is not or substantially not affected. More particular, a material can have such low Zinc leaching capacity if it has a maximum release of 5 μg Zinc ions per day and needle neighbouring part after incubation for 1 day at 25° C. in 1 mL of a 20 mM histidine-HCl, 100 mM arginine-HCl, 30 mM L-methione, 0.02% polysorbate 80, pH 6.0±0.5 aqueous solution. Thereby, the needle neighbouring part of the rigid needle shield is cut into 4 equal sized pieces.

Embodiment 2 is the syringe of embodiment 1, wherein the rigid needle shield is water vapour tight. The effects and advantages provided for by a water vapour tight rigid needle shield as well as of the following preferred embodiments of syringes are explained above in connection with the invention and its preferred embodiments.

Embodiment 3 is a syringe according to embodiment 1 or 2, wherein the rigid needle shield comprises a water vapour tight coat.

Embodiment 4 is a syringe according to embodiments 3, wherein the coat comprises wax, particularly organic wax.

Embodiment 5 is a syringe according to embodiment 3 or 4, wherein the coat comprises a water vapour tight pouch filled with an aqueous fluid.

Embodiment 6 is a syringe according to embodiment 1 or 2, wherein the rigid needle shield comprises a needle neighbouring part being adjacent to the needle which is made of a water vapour tight material.

Embodiment 7 is a syringe according to embodiment 6, wherein the water vapour tight material is ethylene propylene diene methylene based thermoplastic elastomer.

Embodiment 8 is a syringe according to embodiments 6, wherein the water vapour tight material is styrene-butadiene rubber compound free from 2 mercaptobenzothiazole.

Embodiment 9 is a syringe according to any one of the preceding embodiments 1 to 8, wherein the interior of the body is sealed at a side opposite to the needle by a plunger.

Embodiment 10 is a syringe according to any one of the preceding embodiments 1 to 9, wherein the needle is integral with the body.

Embodiment 11 is a syringe according to any one of the preceding embodiments 1 to 10, wherein the pharmaceutical substance is a biopharmaceutical substance.

Embodiment 12 is a syringe according to embodiment 11, wherein the biopharmaceutical substance comprises a protein.

Embodiment 13 is a syringe according to embodiment 12, wherein the substance comprises the protein at a concentration in a range of about 50 mg/ml to about 250 mg/ml.

Embodiment 14 is a syringe according to embodiment 12 or 13, wherein the protein is a monoclonal antibody.

The aspects of the invention mentioned hereinbefore and other aspects will be apparent from and elucidated with reference to the embodiment(s) described hereinafter.

BRIEF DESCRIPTION OF THE DRAWINGS

The syringe and method according to the invention are described in more detail hereinbelow by way of exemplary embodiments and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations), and the spatially relative descriptors used herein interpreted accordingly. Likewise, descriptions of movement along and around various axes includes various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for the reason of lucidity, if in a section of a drawing nor all features of a part are provided with reference signs it is referred to other sections of the same drawing. Like numbers in two or more figures represent the same or similar elements.

Figure 1:
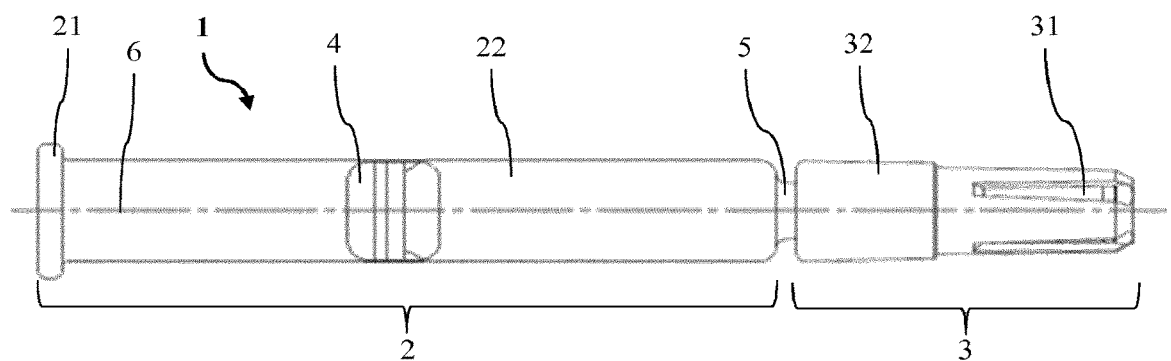
FIG. 1 shows a view on a first embodiment of a needle according to the invention having a rigid needle shield with a water vapour tight elastomeric needle neighbouring part.

FIG. 1 shows a staked-in needle (SIN) pre-filled syringe (PFS) 1 as a first embodiment of a syringe according to the invention. The SIN-PFS 1 has a longitudinal hollow glass body 2 which, at its one end along its longitudinal axis 6, passes over into a needle via a neck 5. At a longitudinal end opposite to the neck 5, the body 2 has an opening. The border of the opening is embodied as finger flange 21.

The interior 22 of the body 2 is delimited in a direction along the axis 6 opposite to the needle by a butyl rubber plunger 4. The plunger 4 seals the interior 22 of the body 2. In the interior 22 a liquid biopharmaceutical substance is arranged which comprises proteins at a concentration in a range between 50 mg/ml and 250 mg/ml.

The needle of the SIN-PFS 1 is protected by a rigid needle shield 3 comprising an elastomeric needle cover 31 as needle neighbouring part and a thermoset cap 32. The rigid needle shield 3 extends from the tip of the needle to the neck 5.

The needle cover 31 is made from either ethylene propylene diene methylene based thermoplastic elastomer or from styrene-butadiene rubber compound free from 2 mercaptobenzothiazole. It directly encases the needle of the SIN-PFS 1.

The cap 32 of the rigid needle shield 3 is comparably solid and resistant to mechanical stress. It encases the needle cover 31 wherein it has plural axial slits widening in a distal direction. Through the slits of the cap 32 the needle cover 31 is accessible. In particular, through the slits of the cap 32 the needle can be sterilized in a common fashion, e.g. by ethylene oxide gas sterilization or the like. Thus, the material of the needle cover 31 is permeable with respect to an appropriate sterilization and in the mean time water vapour tight in the sense of the invention. Furthermore, the material of the needle cover 31 has a low Zinc leaching capacity.

Figure 2:
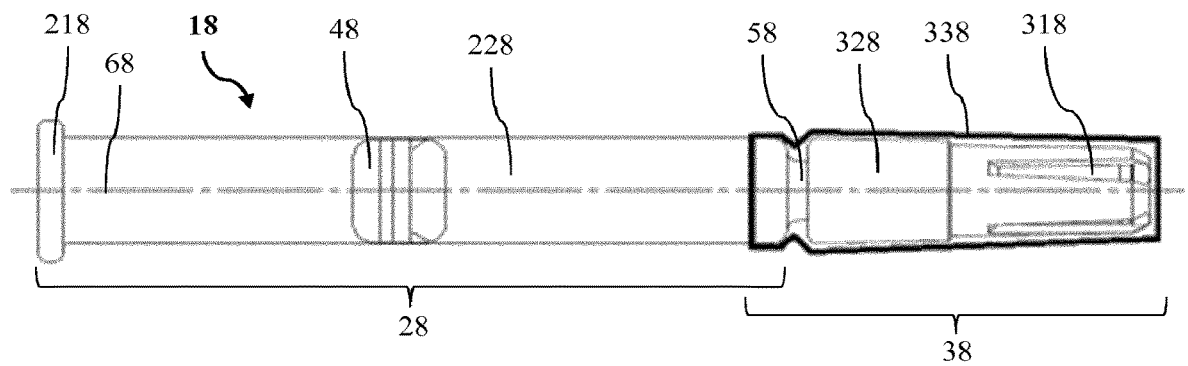
FIG. 2 shows view on a second embodiment of a needle according to the invention having a rigid needle shield with a wax coat.

In FIG. 2 another staked-in needle pre-filled syringe 18 as a second embodiment of a syringe according to the invention is shown. The SIN-PFS 18 has a body 28, a neck 58, a plunger 48, a needle and a longitudinal axis 68 which are identically embodied as the same parts of the SIN-PFS 1 shown in FIG. 1. In particular, the body 28 comprises an identical opening with a finger flange 218 and an identical interior 228 between the plunger 48 and the needle which is filled with a liquid biopharmaceutical substance.

The SIN-PFS 18 further has a rigid needle shield 38 protecting the needle of the SIN-PFS 18. The rigid needle shield 38 comprises an elastomeric needle cover 318 as needle neighbouring part, a thermoset cap 328 and a coat 338. The needle cover 318 is made from a conventional material such as, e.g., polyisoprene. It directly encases the needle of the SIN-PFS 18.

The cap 328 is identically embodied as the cap 32 of the rigid needle shield 3 of the SIN-PFS 1 of FIG. 1. It is covered by the coat 338 made of an organic wax which is arranged on the cap 328, the neck 58 and a section of the body 28. Thus, the rigid needle shield 38 extends from the tip of the needle to the body 28.

For preparing the SIN-PFS 18, it can be obtained in a pre-arranged manner. I.e., the interior 228 of the body 28 of the SIN-PFS 18 is filled with the biopharmaceutical substance and sealed by pushing the plunger 48 through the opening of the body 228, and the needle is encased with the conventional needle cover 318 and needle cap 328. Then the obtained SIN-PFS 18 can be dipped needle down into liquid organic wax up to the section of the body 228. After a short time the SIN-PFS 18 is removed from the liquid wax and the layer adhering on the SIN-PFS 18 is building the coat 338 after cooling and thereby curing.

Figure 3:
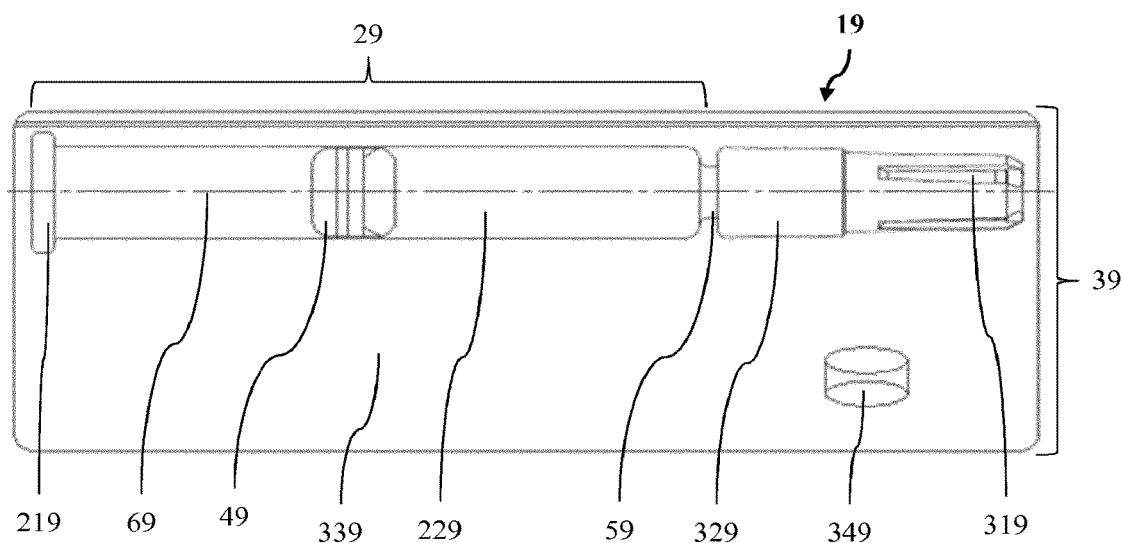
FIG. 3 shows a view on a third embodiment of a needle according to the invention having a rigid needle shield with a pouch filled with an aqueous solution as coat.

FIG. 3 shows a further other staked-in needle pre-filled syringe 19 as a third embodiment of a syringe according to the invention. The SIN-PFS 19 has a body 29, a neck 59, a plunger 49, a needle and a longitudinal axis 69 which are identically embodied as the same parts of the SIN-PFS 1 shown in FIG. 1. In particular, the body 29 comprises an identical opening with a finger flange 219 and an identical interior 229 between the plunger 49 and the needle which is filled with a liquid biopharmaceutical substance.

The SIN-PFS 19 further has a rigid needle shield 39 protecting the needle of the SIN-PFS 19. The rigid needle shield 39 comprises an elastomeric needle cover 319 as needle neighbouring part, a thermoset cap 329 and a pouch 339 as coat. The needle cover 319 is made from a conventional material such as, e.g., polyisoprene. It directly encases the needle of the SIN-PFS 19. The cap 329 is identically embodied as the cap 32 of the rigid needle shield 3 of the SIN-PFS 1 of FIG. 1.

All the parts of the SIN-PFS mentioned hereinbefore are packed in the pouch 339. Thereby, all these parts are hermetically sealed by the pouch 339. Inside the pouch an aqueous solution is arranged which is filled through an inlet 349 of the pouch 339. Thus, the pouch 339 of the rigid needle shield 39 and the aqueous solution completely encase the other parts of the SIN-PFS 19.

For preparing the SIN-PFS 19, it can be obtained in a pre-arranged manner as described above in connection with the preparation of the SIN-PFS 18 of FIG. 2. Then the obtained SIN-PFS 19 can be wrapped in the pouch 339 and the aqueous solution can be provided into the inside of the pouch 339 via the inlet 349. For obtaining or gathering the aqueous solution a matrix such as a cotton ball can be provided inside the pouch 339. Thereby, the pouch 339 together with the aqueous solution forms the coat.

In the following, some examples of syringes according to the invention are defined, evaluated and compared to each other. Thereby, Example 1 is a prior art syringe as reference. The reference syringe is a staked-in needle pre-filled glass syringe with a rigid needle shield having an inner core made from polyisoprene elastomer (formulation 4800, Stelmi) and an outer thermoset cover. The interior of the reference syringe is filled with a concentrated Tocilizumab (available from or provided by F. Hoffmann La Roche AG, INN) formulation as biopharmaceutical substance using a tray filler (Inova V122) with a target extractable volume of 0.959 mL.

For obtaining the concentrated Tocilizumab formulation an initial Tocilizumab formulation (180 mg/ml Tocilizumab, 20 mM L-histidine-HCL, 30 mM L-methionine, 100 mM L-arginine-HCL, 0.02% polysorbate 80, pH 6.0) is concentrated to a Tocilizumab concentration of 189 mg/mL Tocilizumab using tangential flow filtration process with a semi-permeable membrane with 30 kD molecular weight cut-off. The concentrated Tocilizumab solution is sterile filtered through 0.22 μm polyvinylidene difluoride (PVDF) filter membrane.

Example 2 is a staked-in needle pre-filled glass syringe with a rigid needle shield having an inner core made from polyisoprene elastomer (formulation 4800, Stelmi) and an outer thermoset cover. The interior of the syringe is filled with the same concentrated Tocilizumab formulation as mentioned above using a tray filler (Inova V122) with a target extractable volume of 0.959 mL. The syringe is co-packed in a water vapour tight aluminium pouch filled with an aqueous solution as water vapour tight coat.

The aluminium foil pouch is made of adhesive laminate of 12 μm printable polyester, 20 μm white polyethylene, 9 μm aluminium foil and 65 μm CleanPeel™ peelable polyethylene sealant layer (240×240 mm), with a WVTR of less than 0.01 g/(m2×day) (at 38° C./90%/rh). PFS were put in aluminium foil pouch together with a 5×5 cm cotton tissue adsorbing 5 mL pure water, followed by heat sealing (170-200° C.) of the aluminium pouch.

Example 3 is a staked-in needle pre-filled glass syringe with a rigid needle shield having an inner core made from ethylene propylene diene methylene (EPDM) based thermoplastic elastomer (formulation 8550, Stelmi) as vapour tight needle neighbouring part and an outer thermoset cover. The interior of the syringe is filled with the same concentrated Tocilizumab formulation as mentioned above using a tray filler (Inova V122) with a target extractable volume of 0.959 mL.

Example 4 is a staked-in needle pre-filled glass syringe with a rigid needle shield having an inner core made from styrene-butadiene rubber compound free from 2-mercapto-benzothiazole (MBT) (formulation FM30, Datwyler) as vapour tight needle neighbouring part and an outer thermoset cover. The interior of the syringe is filled with the same concentrated Tocilizumab formulation as mentioned above using a tray filler (Inova V122) with a target extractable volume of 0.959 mL.

Example 5 is a staked-in needle pre-filled glass syringe with a rigid needle shield having an inner core made from polyisoprene elastomer (formulation 4800, Stelmi) and an outer thermoset cover. The interior of the syringe is filled with the same concentrated Tocilizumab formulation as mentioned above using a tray filler (Inova V122) with a target extractable volume of 0.959 mL. The thermoset cover of the rigid needle shield is coated with a water vapour tight material such as wax after filling of the drug product solution.

All above examples of pre-filled syringes are stored at 40° C./25% rh for up to 1 months.

The rigid needle shield (RNS) inner rubber material or needle neighbouring part of respective RNS variants are cut into four pieces and incubated with 1 mL Tocilizumab solution (180 mg/mL, 20 mM L-histidine-HCL, 30 mM L-methionine, 100 mM L-arginine-HCL, 0.02% polysorbate 80, pH 6.0) in a sealed glass vial at 5° C., 25° C. and 40° C., respectively. After 4 weeks, 8 weeks and 13 weeks incubation, samples are analysed with respect to dynamic viscosity.

Figure 4:
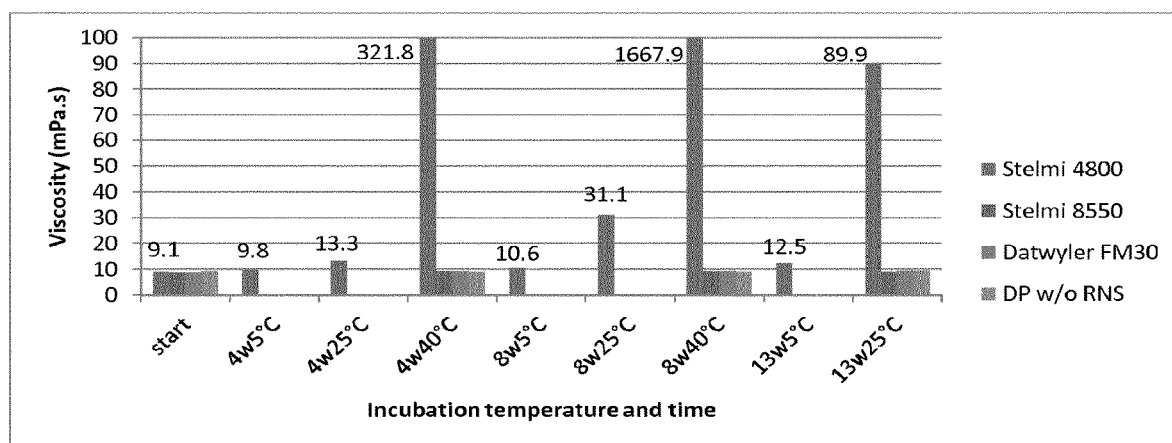
FIG. 4 shows a graphical view representing viscosity vs. incubation temperature and time of plural examples of syringes according to the invention.

As shown in FIG. 4, after four weeks incubation at 40° C. and 8 weeks incubation at 25° C. with RNS rubber formulation 4800 from Stelmi, the viscosity of Tocilizumab formulation viscosity increased significantly and the sample solution converted to a semi-solid gel-like material. Rubber pieces made of rubber formulations 8550 from Stelmi and FM30 from Datwyler show no increase of viscosity of Tocilizumab formulations and behaved like to the Tocilizumab sample without RNS rubber pieces (DP w/o RNS).

The following Table summarizes one month needle clogging data. Reference Example 1 shows a clogging rate set to 100%. Example 2 demonstrates that appropriate packaging prevents needle clogging completely after one month storage at 40° C./25% rh. Example 3 demonstrates that an alternative RNS variant with smaller water vapour transmission rate and improved material compatibility reduces needle clogging significantly compared to Example 1. Example 4 does not decrease clogging rate in comparison to Example 1, although the compatibility with the Tocilizumab (INN) formulation is demonstrated in the RNS incubation study. Example 5 is expected to show similar results as Example 2.

TABLE

Needle clogging rate after 1 month storage at 40° C. 25% rH
(sample size is 59 PFS)

| Example | RNS type | Needle ID | Package | Comments | Clog rate % after 1 month at 40° C./ 25% rh |
|---|---|---|---|---|---|
| 1 | Stelmi 4800 | 27G RW | no | Reference | 100% |
| 2 | Stelmi 4800 | 27G RW | Aluminum pouch + water wet cotton | Add. Secondary packaging plus 100% rel. humidity inside | 0% |
| 3 | Stelmi 8550 (TPE) | 27G RW | no | New RNS material | 1.7 |
| 4 | Datwyler FM30 | 27G TW | no | New RNS material | 98.7% |
| 5 | Stelmi 4800 | 27G RW | RNS is coated | RNS surface coating reduces WVTR significantly | |

This description and the accompanying drawings that illustrate aspects and embodiments of the present invention should not be taken as limiting—the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims.

In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A staked needle pre-filled syringe system comprising:
    a longitudinal body with an interior in which a pharmaceutical substance is arranged;
    a needle staked in to one longitudinal end of the body via a neck of the body; and
    a rigid needle shield encasing the needle, wherein the rigid needle shield includes a coat comprising a water vapour tight pouch filled with an aqueous fluid.

2. The syringe system of claim 1, wherein the pouch is formed of aluminum.

3. The syringe system of claim 1, further including a matrix configured for holding the aqueous fluid.

4. The syringe system of claim 1, wherein a needle neighboring part of the rigid needle shield being adjacent to the needle has a low leaching capacity.

5. The syringe system of claim 4, wherein the low leaching capacity is a low Zinc leaching capacity.

6. The syringe system of claim 5, wherein the needle neighboring part of the rigid needle shield has a maximum release of 5 µg Zinc ions per day after incubation for 1 day at 25° C. in 1 mL of a 20 mM histidine-HCl, 100 mM arginine-HCl, 30 mM L-methione, 0.02% polysorbate 80, pH 6.0±0.5 aqueous solution.

7. The syringe system of claim 1, wherein the interior of the body is sealed at a side opposite to the needle by a plunger.

8. The syringe system of claim 1, wherein the needle is integral with the body.

9. The syringe system of claim 1, wherein the pharmaceutical substance is a biopharmaceutical substance.

10. The syringe system of claim 9, wherein the biopharmaceutical substance comprises a protein.

11. The syringe system of claim 10, wherein the biopharmaceutical substance comprises the protein at a concentration in a range of about 50 mg/ml to about 250 mg/ml.

12. The syringe system of claim 1, wherein the rigid needle shield includes a cap being resistant to mechanical stress.

13. The syringe system of claim 12, further comprising an elastomeric needle cover, wherein the cap encases the elastomeric needle cover and includes a plurality of axial slits permeable to gas sterilization.

* * * * *